United States Patent
Mencanin et al.

(10) Patent No.: US 12,357,471 B2
(45) Date of Patent: Jul. 15, 2025

(54) TREATMENT OF SPINAL INJURY WITH MULTIFOCAL POLYMER

(71) Applicant: DIRECT COMPONENTS, INC., Cheyenne, WY (US)

(72) Inventors: Steve Mencanin, Lake Forest, CA (US); Frank Miller, Manassas, VA (US)

( * ) Notice: Subject to any disclaimer, the term of this patent is extended or adjusted under 35 U.S.C. 154(b) by 157 days.

(21) Appl. No.: 17/957,733

(22) Filed: Sep. 30, 2022

(65) Prior Publication Data

US 2024/0065859 A1 Feb. 29, 2024

Related U.S. Application Data (60) Provisional application No. 63/401,459, filed on Aug. 26, 2022.

(51) Int. Cl.
| | | |
|---|---|---|
| *A61F 2/46* | (2006.01) | |
| *A61B 17/17* | (2006.01) | |
| *A61F 2/44* | (2006.01) | |
| *A61B 17/02* | (2006.01) | |

(52) U.S. Cl.
CPC ........ *A61F 2/4611* (2013.01); *A61B 17/1757* (2013.01); *A61F 2/4455* (2013.01); *A61B 2017/0256* (2013.01)

(58) Field of Classification Search
CPC ....... A61F 2/4611; A61F 2/4455–2/447; A61F 2/4405; A61F 2/442; A61F 2002/444
See application file for complete search history.

(56) References Cited

U.S. PATENT DOCUMENTS

| | | | |
|---|---|---|---|
| 2007/0179620 A1* | 8/2007 | Seaton, Jr. | A61F 2/4611 623/17.12 |
| 2008/0183192 A1* | 7/2008 | Saal | A61B 17/320783 600/129 |
| 2010/0152854 A1* | 6/2010 | Slivka | A61B 17/7071 623/17.12 |
| 2013/0103155 A1* | 4/2013 | Tornier | A61F 2/4611 623/17.16 |
| 2013/0304212 A1* | 11/2013 | VonGunten | A61F 2/441 623/17.16 |
| 2016/0278822 A1* | 9/2016 | Davis | A61F 2/4611 |
| 2019/0307572 A1* | 10/2019 | McCormack | A61B 17/025 |
| 2020/0215224 A1* | 7/2020 | Saber | A61L 26/0066 |

OTHER PUBLICATIONS

Spiegl et al., Traumatic Fractures of the Thoracic Spine, journal, last accessed Sep. 30, 2022, https://pubmed.ncbi.nlm.nih.gov/32392598/, 10 total pages.
Stergar et al., "Intervertebral disc tissue engineering: A brief review", vol. 19 No. 2 (2019), https://www.bjbms.org/ojs/index.php/bjbms/article/view/3778, last accessed Sep. 30, 2022, 19 total pages.
Kenneth R. St. John, The Use of Polyurethane Materials in the Surgery of the Spine: A Review, The Spine Journal (2014), https://linkinghub.elsevier.com/retrieve/pii/S1529943014008444, last accessed Sep. 30, 2022, 36 total pages.
Bowles et al., "Biomaterials for Intervertebral Disc Regeneration and Repair", Biomaterials. Jun. 2017 ; 129: 54-67, https://pubmed.ncbi.nlm.nih.gov/28324865/, last accessed Sep. 30, 2022. 31 total pages.

* cited by examiner

*Primary Examiner* — Julianna N Harvey
*Assistant Examiner* — Angel Roberto Mora-Velazquez (57) ABSTRACT

There is disclosed a treatment of spinal trauma with a novel polymer solution.

14 Claims, 2 Drawing Sheets

TREATMENT OF SPINAL INJURY WITH MULTIFOCAL POLYMER

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the Patent and Trademark Office patent files or records, but otherwise reserves all copyright and trade dress rights whatsoever.

RELATED APPLICATION INFORMATION

The present application claims priority to U.S. Provisional Application No. 63/401,459 filed Aug. 26, 2022 entitled "THE REMEDY FOR ABNORMAL SPINAL DISC BY USE OF MULTIFOCAL POLYMERS" of which is incorporated herein by reference in its entirety.

BACKGROUND

Field

This disclosure relates to the use of specific polymers to treat various spinal injuries including injuries due to friction of spinal tissue over time and trauma.

Description of the Related Art

Injuries of the spinal cord remain some of the most difficult medical conditions to treat. Current surgeries often require expensive material that break down over time or worse yet, cause other parts of spinal tissue to deteriorate. Patients are constantly left with pain despite treatment due to angered nerves and are often left having to go back to surgery later. The reason for these ailments boils down to a lack of material that can be resilient through time and not affect healthy spinal tissue. The present disclosure demonstrates a solution to this problem.

Table 1 lists a selection of the properties of UHMWPE, PEEK, and a subset of some of the polyurethanes that are currently used in spinal surgery. The problem with these polymers is that they often take too long to cure, and after a year or so begin to lose their flexibility. Worse yet, some immune responses have been known to attack these polymers which leads to inflammation, defeating the purpose of putting them into the spine to begin with.

DETAILED DESCRIPTION

Figure 1:
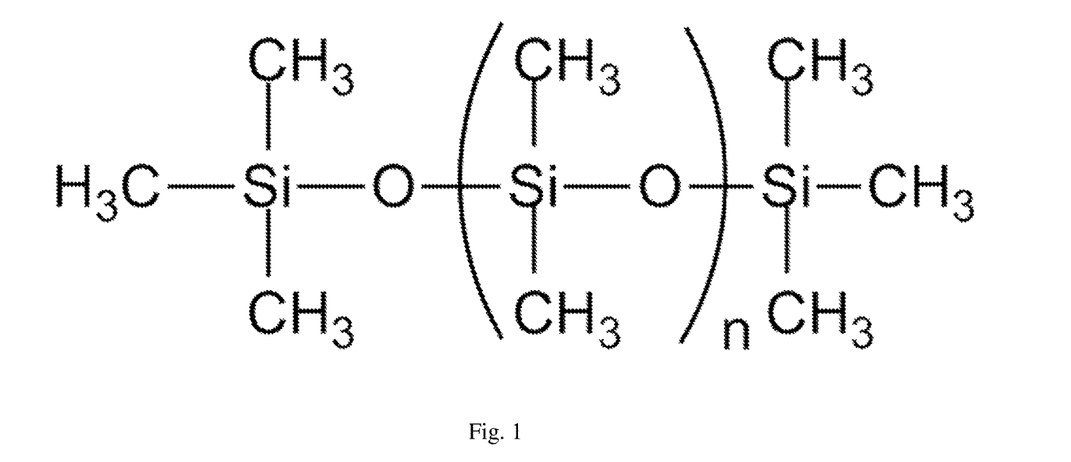
FIG. 1 is a drawing of a chemical structure of Polydimethylsiloxane.
Figure 2:
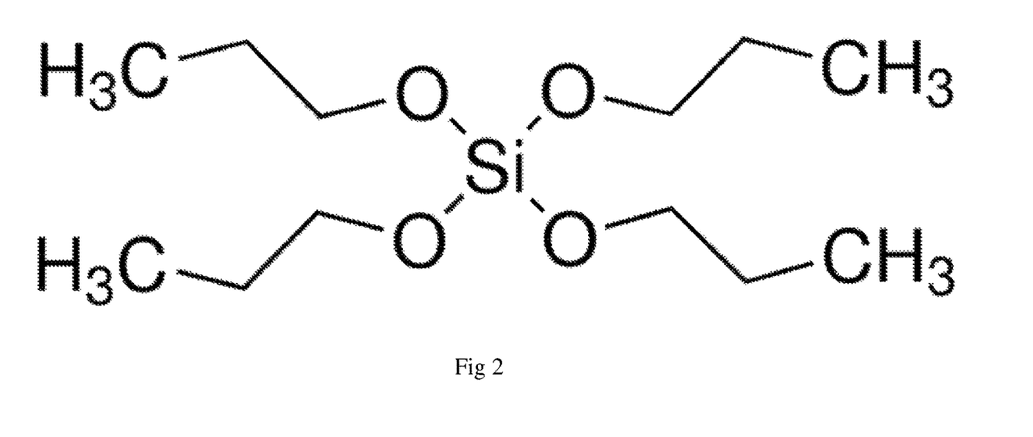
FIG. 2 is a drawing of a chemical structure of Tetrapropyl orthosilicate (also referred to as Tetrapropoxysilane or $(CH_3CH_2CH_2O)_4Si$.

The spine is composed of intervertebral discs and interspinous and longitudinal ligaments. These structures are partially elastomeric and/or viscoelastic. From a mechanical standpoint, these elements allow for the mechanical movement of the bony parts of the spine. Due to trauma as well as growing older often times the bony parts of the spine as well as discs may be damaged.

Throughout the last century, doctors and medical professionals have experimented with different materials to replace broken parts of the spine and replace portions of the spine altogether. Some have tried using hard polymeric devices to replace the intervertebral discs and/or to create fusion masses to replace discs and/or vertebral bodies. These methods leave much to be desired because they change the load transfer characteristics of the spine and the range of motion of segments of the spine. This leads to patients with limited movement and sometimes prolonged nerve damage. Worse yet, patients often need to go in for surgery several times afterwards.

Samaratin® is a polymerizable composition with applications for wound healing, blood loss, and fusing skin. Throughout this disclosure it may be referred to as polymerizable matrix, S-polymer, or S-gel. S-polymer may come in various forms and have different polymers making it up. Commercially available Samaratin® available via Direct Components Inc. may also be considered S-polymer. S-polymer may come in a form of compositions that are silicone elastomer compositions comprising two or more separate components. A first component may include a catalyst and a second component may include a cross-linker. When the two components are combined or mixed, a temporary or permanent seal quickly forms and may adhere to spongy tissue including bone or skin.

A therapeutically effective amount of a drug or treatment may be suspended or otherwise incorporated into one or more components of the S-polymer. For example, a drug having a sustained release property can be incorporated into the polymerizable composition, and can be effective to deliver the drug to an area near the attachment site over a prolonged period of time. Stem cells or bone growing stimulant may also be incorporated into the S-polymer. Bone graft may also be put into S-polymer to facilitate spinal surgery.

S-polymer may have a work time sufficient such that the two or more components (polymers, catalyst or other chemicals) may be delivered simultaneously to a target site without clogging or polymerizing before being exposed to bone or other tissue. In other instances, the two or more components composing the S-polymer may be delivered to a target site sequentially to further prevent unwanted and premature curing.

In other instances, a base composition could be delivered to a target site prior to the S-polymer. The base component could prevent or block a flow of the S-polymer, enhance adhesion of S-polymer to somatic cells, or minimize an adhesion of the S-polymer to a medical device or delivery system delivering the S-polymer. For example, the base composition could comprise a composition that polymerizes upon exposure to blood or the vessel outside of the catheter to form a temporary seal that spontaneously or otherwise dissolves. The temporary seal could block a flow of the polymerizable composition until the more permanent seal is formed, and subsequently be dissolved.

When S-polymer forms a seal, the seal may be inelastic, elastic or semi-elastic. For example, some S-polymer compositions when fully cured may have an elasticity at break of between 120-1000% (e.g., between 400 and 800% or between 450-600%) and mimic the elasticity of the target site to reduce the likelihood of dislodgment or tear. Some contemplated compositions for forming a stent can have the same, a greater inelasticity, or a reduced inelasticity. For use with the spine a more elastic form should be used.

The presence of blood accelerates the cure time of the S-polymer. When some S-polymer formulations were placed on an injury where blood was exposed, the cure time was found to decrease by about 15 seconds (compared to cure time on skin without the presence of blood). It is hypothesized that the temperature of the blood and its iron content may speedup the cure time of the S-polymer. Additionally, the S-polymer has been found to adhere to the tissue even in the presence of blood, and infuse approximately 0.25 mm-5 mm into surrounding tissue and vessels. This infusion is useful for treatment of bones in the spine. Spinal tissue contains spongy bone which S-polymer can fill the crevices of which enhances structural integrity. S-polymer can infuse further into the tissue and vessels, for example up to 1 foot or even further. Therefore, S-polymer can secure a target site of a vessel, optionally without causing an embolus where desired (e.g., when implanting a stent). The S-polymer composition can be removed with the removal of a tumor or arteriovenous malformations where desired. Indeed, this is a main reason why S-polymer is superior to other polymers, metals, ceramics, and other spinal instrument compositions. The removal of these other instruments and compositions may cause damage to the spinal tissue, whereas S-polymer causes minimal to no damage.

S-polymer scan comprise a short term temporary seal, a long term temporary seal, or a permanent seal. For example, S-polymer may remain adhered to an inner or outer surface of a vessel (or a stent placed in the vessel) or bone for a period of at least 1 hour (e.g., at least 3 hours, at least 5 hours, at least 8 hours, at least 10 hours, at least 12 hours, at least 15 hours, at least 20 hours, at least 1 day, at least 2 days, at least 3 days, at least 4 days, at least 5 days, at least 1 month, at least 1 year, between 1-10 days, between 1-10 weeks, between 1-10 years, or even longer). Other compositions of S-polymers may last more a lifetime (more than 80 years).

S-polymer may result in a cured seal having sufficient elasticity to allow the user to move around comfortably without dislodging the seal or damaging the blood vessel. S-polymer may be introduced into a vessel and removed without causing damage to the vessel. S-polymer may be left in the vessel without causing damage to the patient. The polymerizable composition is typically odorless, non-toxic, hypoallergenic, compatible with other treatments, bacteriostatic, non-temperature sensitive, and removable as a single piece, or in sections, after curing.

S-polymer may comprise a one part system, for example, where the polymerizable composition is temperature or light activated. S-polymer may comprise a multi-part system, for example, where a catalyst and a cross-linking component must be separated to prevent premature curing. One variety of S-polymer comprises a polymerizable composition comprises a two-part elastomer system that cures at room or body temperature and includes (a) a first formulation including a polymer and catalyst (e.g., siloxane polymer and platinum catalyst), and (b) a second formulation comprising a polymer and a crosslinker. One or both of the formulations could include one or more of a filler, a thixotropic agent, an adhesion promoter, and a cure inhibitor to control the cure kinetics.

Dual chambered syringe are great for storing and using S-polymer because if formulated and packaged correctly crosslinking cannot occur until the two components are mixed together (e.g., delivered separately via a catheter or syringe to the target site, or delivered as a mixture).

S-polymer may be a silicone polymer (siloxane polymer) with a polymer backbone of alternating silicone and oxygen atoms (i.e., siloxane bonds), and hydrocarbon (saturated, unsaturated, aromatic) organic side groups such as methyl, phenyl or vinyl, or a hydrogen attached to the silicon atoms. The siloxane polymer can comprise between 20-100 wt %, more preferably at least 50 wt %, and even more preferably at least 70 wt % (e.g., between 75-85 wt %, between 78-82 wt %) of the polymerizable composition (i.e., of the combined two part formulation where the catalyst and crosslinker are combined).

Where PDMS is used, it can be a linear polymer made up of repeating Si—O—Si linkages and a reactive vinyl group on both ends of the polymer chain. There may be organic side groups such as dimethyl bonded to every silicone molecule the backbone of the polymer. Siloxane polymers can also be substituted with diphenyl, methylphenyl, trifluoropropyl, or any combination thereof. Some exemplary siloxanes include oligosiloxanes, polydimethylsiloxane (PDMS), vinyl-endblocked polydiphenyl siloxane, vinyl-endblocked polymethylphenylsiloxane, vinyl-endblocked trifluoropropyl siloxane, vinyl-endblocked polydiethyl siloxane, trimethyl-endblocked methylvinyl polydimethylsiloxane, trimethyl-endblocked methylvinyl polydiphenylsiloxane, trimethyl-endblocked methylvinyl polymethylphenylsiloxane, trimethyl-endblocked methylvinyl polytrifluoropropylsiloxane, and trimethyl-endblocked ethylvinyl polydimethylsiloxane. Contemplated siloxanes can be optically clear, non-toxic and non-flammable.

A plethora of suitable chain lengths of the siloxane polymer (which may comprise the entire S-polymer) are possible, including between 10-2,500 repeating units long, between 200-1,000 repeating units long, or between 300-400 repeating units long (e.g., 340-360). This may equate to a molecular weight of 26,000 Daltons. A polymer can include a main chain formed primarily of organosiloxane units. Among the silicone compounds contemplated, some may display both curing and adhesive properties, for example depending on the proportion of silicone or whether they are used with a particular additive. Changing the proportion of silicon to be either higher or lower may change the adhesive as well as flexibility of the S-polymer.

In some versions of S-polymer the polymer may be a siloxane, and a crosslinker may be a siloxane crosslinker such as a methyl-hydrogen crosslinker. The crosslinker may comprise between 0.1-50 wt %, between 0.1-10 wt %, and more preferably between 1-5 wt % (e.g., 2 wt %) of the polymerizable composition. An exemplary siloxane crosslinker used in some contemplated compositions is a small chain polymer that is trimethyl end blocked, making the ends of the chain non-functional. All suitable chain lengths of the crosslinker are contemplated, including for example, between 1-100 repeating units, more preferably between 1-50 units, and more preferably between 5-15 units (e.g., 10 units wherein the molecular weight is 800 Daltons). Along the backbone of the crosslinker can be reactive methyl-hydrogen side groups which can comprise between 1-99 mole %, more preferably between 20-80 mole %, and more preferably between 40-60 mole % (e.g., 50 mole %) of the crosslinker. The remaining mole % can comprise dimethyl side groups. Where each of the methyl-hydrogen side groups and the dimethyl side groups make up approximately 50 mole %, approximately half of the repeating units of the crosslinker will be dimethyl, and approximately half will be methyl hydrogen.

Other appropriate crosslinkers include hydride-endblocked polydimethylsiloxane, hydride-endblocked methylhydrogen polysiloxane, trimethyl-endblocked methylhydrogen methylvinyl polysiloxane, trimethyl-endblocked 100 mole % methylhydrogen polysiloxane, hydride-endblocked polydiphenylsiloxane, and hydride-endblocked phenylhydrogen polysiloxane. The catalysts of polymerizable formulations making S-polymer can comprise a peroxide, platinum, tin, a combination thereof, or other suitable catalyst. An exemplary platinum catalyst for hydrosilylation reactions can comprise a complex of platinum with a vinyl siloxane acting as a ligand. An example of this is the Karstedt's catalyst. Other contemplated catalysts include, rhodium complex in vinyl silicone fluid, organotin catalyst such as dibutyltin dilaurate, stannous octoate, dibutyltin diacetate, peroxide catalysts such as benzoyl peroxide, 2,4 dichlorobenzoyl peroxide, dicumyl peroxide, 2,5-Dimethyl-2,5-di(tert-butylperoxy)hexane.

The catalyst may be present in the formulation in any suitable amount, for example, between 0.001-10 wt % (of the combined two part formulation where the catalyst and crosslinker are combined), more preferably between 0.01 and 1 wt %, and more preferably between 0.07 and 0.13 wt % (e.g., 0.1 wt %) of the polymerizable composition, and can include between 1-250 ppm, between 5-70 ppm, more preferably between 15-60 ppm (e.g., 30 ppm) of pure platinum. The platinum catalyst will preferably be separated from the crosslinker until placed within, or on, the injury. Alternatively, or additionally, the platinum catalyst may be combined with the crosslinker no more than 10 minutes, no more than 5 minutes, no more than 3 minutes, and preferably no more than 1 minute or 0.5 minute prior to being placed within, or on, the injury or spine. Alternatively, or additionally, the component or formulation comprising the platinum catalyst can be placed within the injury before or after the formulation or component comprising the crosslinker is placed within, or on, the injury. As discussed in more detail below, a base component (e.g., spray) comprising the same or different catalyst could be applied prior to any of the first formulation (including the platinum catalyst) and the second formulation (including the crosslinker).

Below is a chart of polyurethanes and their attributes not as favorable as S-polymer for spinal procedures

| Material | Flexural Modulus (MPa) | Tensile Strength (MPa) | Hardness Scale | Hardness | Elongation to Break (%) |
|---|---|---|---|---|---|
| Ultra High Molecular Weight Polyethylene | 500 (Tensile) | 50 | Shore D | 65D | 450 |
| Poly(Ether Ether Ketone) | 4000 | 75 | Rockwell R | 126 $HR_R$ | 25-30 |
| Poly Carbonate Urethane 80A | 28 | 45 | Shore A | 80A | 525 |
| Poly Carbonate Urethane 90A | 42 | 55 | Shore A | 90A | 400 |
| Poly Carbonate Urethane 55D | 48 | 60 | Shore D | 55D | 360 |

Below is a chart of exemplary polymers that may be found in S-polymer.

Tetrapropoxysilane
3-aminopropropyltrimethoxysilane
Tris(2-methoxyethoxy)(vinyl)silane
Vinyltriethoxysilane
Tetrakis(2-methoxyethyl)ester
Thmethoxy-7-octenylsilane
N-(triethoxysilylpropyl)-O-polyethylene oxide urethane
Vinyl endblockedpolydimethyl
Trimethyl endblockedmethyl-hydrogen siloxane polymer
1,3,5,7-tetramethyl-1,3,5,7-tetravinyl-cyclotetrasiloxane Where a filler is included in the polymerizable formulation, an exemplary filler includes amorphous fumed silica having a surface area of between 100-300 m2/gram (e.g., approximately 200 m2/gram). Other contemplated fillers include fumed silica with low surface area (e.g., 100 m2/gram), fumed silica with high surface area (e.g., 400 m2/gram), precipitated silica, diatomaceous earth, titanium dioxide, zinc oxide, barium sulfate, colloidal silica, and boron nitride. The filler may comprise between 0-80 wt %, more preferably between 5-35 wt % and even more preferably between 10-23 wt % (e.g., 16 wt %) of the combined two part formulation where the catalyst and crosslinker are combined. The surface of the silica can be treated with trimethyl silyl groups so that it is more soluble with the polymer. The filler can comprise between 0-80 wt %, more preferably between 5-35 wt % and even more preferably between 10-23 wt % (e.g., 16 wt %) of the combined two part formulation where the catalyst and crosslinker are combined. The surface of the silica can be treated with trimethyl silyl groups so that it is more soluble with the polymer.

Suitable adhesion promoters can also be included in the polymerizable composition to increase the bond strength of the adhesive (polymerizable composition or seal) to the substrate (inner wall of the vessel) as curing occurs. Tetrapropoxysilane is an exemplary adhesion promoter commonly used in silicone primers. Without wishing to be bound by any particular theory, the applicant contemplates that the reactive silane may form hydrogen or even covalent bonds with the vessel. The adhesion promoter, when included in the polymerizable composition, can comprise between 0.01-10 wt %, between 0.1 and 5 wt %, and more preferably between 0.4 and 1.2 wt % (e.g., 0.8 wt %) of the polymerizable composition.

Other contemplated crosslinkers include hydride-endblocked polydimethylsiloxane, hydride-endblocked methylhydrogen polysiloxane, trimethyl-endblocked methylhydrogen methylvinyl polysiloxane, trimethyl-endblocked 100 mole % methylhydrogen polysiloxane, hydride-endblocked polydiphenylsiloxane, and hydride-endblocked phenylhydrogen polysiloxane.

The filler can comprise between 0-80 wt %, more preferably between 5-35 wt % and even more preferably between 10-23 wt % (e.g., 16 wt %) of the combined two part formulation where the catalyst and crosslinker are combined. The surface of the silica can be treated with trimethyl silyl groups so that it is more soluble with the polymer. Bone graft from a patient may be added at this point in the S-polymer making process as well.

The filler can comprise between 0-80 wt %, more preferably between 5-35 wt % and even more preferably between 10-23 wt % (e.g., 16 wt %) of the combined two part formulation where the catalyst and crosslinker are combined. The surface of the silica can be treated with trimethyl silyl groups so that it is more soluble with the polymer.

The filler can comprise between 0-80 wt %, more preferably between 5-35 wt % and even more preferably between 10-23 wt % (e.g., 16 wt %) of the combined two part formulation where the catalyst and crosslinker are combined. The surface of the silica can be treated with trimethyl silyl groups so that it is more soluble with the polymer.

It is also contemplated that inert pigments can be suspended in the polymerizable formulations without leaching. The inert pigments could advantageously allow a surgeon or physician to visualize a tumor while surgically removing it.

The pigments used could contrast with blood and surrounding tissue to allow for faster and more effective removal of the tumor and improved outcome for the patient. Some contemplated powdered pigments can advantageously be broken down to a size of less than 20 microns, more preferably less than 15 microns to allow for even distribution or dispersion throughout the polymerizable formulation. Additionally or alternatively, concentrated liquid or gum color pigments can be added to one or more components of the polymerizable formulation.

Radio opaque or other particles (e.g., barium sulfate, zirconium dioxide) could be suspended or otherwise incorporated into the polymerizable formulations such that the cured seal can be detected by X-ray, computed tomography scans, ultrasound imaging or MRI scans during the embolization or implantation procedure. In some preferred embodiment, at least 8 wt %, more preferably at least 10 wt % (e.g., at least 11 wt %, between 8-50 wt %, between 10-20 wt %) is included in the combined two part polymerizable formulation for detection by X-ray. The radio opaque particles could be added to the polymerizable formulation in any commercially suitable matter, and could even be pre-mixed with one or more of its components. For example, the radio opaque particles could be mixed in with the first formulation component, second formulation component, a silicone polymer, a platinum catalyst, a crosslinker, an adhesion promoter, a cure inhibitor, a filler, a thixotropic agent, or any combination thereof.

It should be appreciated that the polymerizable formulations presented herein provide several advantageous effects including the potential to reduce the time required for tumor removal, enhance visualization of the tumor and surrounding vital structures prior to, during and after surgery, and provide a non-toxic seal whose mechanical and chemical properties can be modified pre-cure to provide a temporary or permanent polymerizable implant within selected blood vessels.

It is contemplated that the first and second formulations can react with each other at various temperatures, including for example at temperatures between −20 and 80 degrees Celsius, more typically between 0 and 60 degrees Celsius, and even more typically between 10 and 50 degrees Celsius, or around 35-40 degrees Celsius (body temperature). For example, it is contemplated that the formulations will be capable of reacting together to form a seal within a blood vessel and in the presence of blood by a hydrosilylation reaction or a condensation reaction, or a crosslinking reaction in the presence of a peroxide.

A complete seal can be formed within 20 minutes, within 10 minutes, more preferably within five minutes, within three minutes, within two minutes, or even within one minute. The S-polymer for use with spinal procedures may cure in 30 seconds or less. The seal can be any suitable size and shape, depending on the type of vascular disease.

Upon full curing, the seal can have a hardness sufficient to prevent unwanted flowing of the seal. For example, the seal can have a hardness of at least 10 on the Shore 00 durometer scale, at least 10 on the Shore A scale, a hardness of between 0 on the Shore 00 durometer scale and 40 on the Shore A durometer scale, a hardness of between 10 on the Shore 00 durometer scale and 30 on the Shore A durometer scale, a hardness of between 15-25 on the Shore A durometer scale, or a hardness of between 18-22 on the Shore A durometer scale. The work time of the polymerizable composition can be approximately half of the cure time (e.g., about sixty seconds where the cure time is about two minutes).

Additionally or alternatively, the seal can have an elasticity that allows for movement and stretching of the blood vessel without compromising the seal or causing damage to the vessel. For example, some contemplated compositions will have an elasticity at break of at least 120%, more preferably at least 200%, and more preferably at least 250% (e.g., between 120-1000%, between 400 and 800%, between 450-600%). As used herein, the term "% elasticity at break" refers to the extension of a length of a cured seal from an unstretched and normal configuration before tearing at room temperature, wherein the cured seal has a thickness of between 3-5 mm in the unstretched, normal configuration. For example, where a cured seal has an at least 180% elasticity at break, the cured seal, when normally having a thickness of between 1-25 mm, can be stretched to at least 180% of its length before tearing (e.g., from 10 mm to at least 18 mm before tearing). Viewed from a different perspective, the seal can have a tensile strength that allows significant force to be applied while maintaining its integrity (e.g., between 100-2000 psi, between 200-800 psi, between 400-650 psi).

Surgery to repair the function of connective tissue of the spinal column is important to patients with injuries or degenerative back conditions. Among the materials used as adjuncts to the surgery being performed are autograft tissues, metals (titanium and stainless steel mostly) allograft tissues, metals, and ceramics. Some medical procedures have used including ultra-high molecular weight polyethylene (UHWPE), poly(etheretherketone) (PEEK), and polyurethanes. The family of Polyurethanes have been used because of their elastomeric properties, which may be tailored by varying the composition of the monomer units and the size of the blocks of the dissimilar monomers within the polymer chain.

The spinal column or backbone is one of the most important parts of your body it provides the main support allowing humans to stand upright bend and twist 33 individual bones interlock with each other to form the spinal column the vertebrae are numbered and divided into regions C1 through C7 cervical vertebrae form the neck support the head and neck and allow humans to nod and shake the head. T1 through T12 which comprise the 12 vertebrae that are joined by ribs to form your rib cage. L1 through L5 lumbar are the five sturdy lumbar vertebrae that carry most of the weight of the upper body and provide a stable center of gravity when a human moves. The five vertebrae of the sacrum and four of the coccyx are fused and make up the back wall of the pelvis. In the event the sacrum and coccyx have holes, trauma or cracks S-polymer may be used to fill in any cavity. Between each of the moveable vertebrae is located the intervertebral discs. Intervertebral discs may be damaged through use or trauma, and when supplemented with S-polymer may allow a patient to regain function. The intervertebral discs consist of a thick outer layer with a criss-crossing fibrous structure annulus that surrounds the soft gel-like center. The soft gel-like center and annulus may be replaced or supplemented with S-polymer. The nucleus discs function like a shock absorbing spring, the annulus pulls the vertebral bodies together against the elastic resistance of the gel-filled nucleus. S-polymer may be added to the fibrous structure of the annulus for therapy and support. When a human bends the nucleus acts like a ball bearing allowing the vertebral bodies to roll over the incompressible gel. Over time, the vertebral bodies may wear down due to trauma or old age. S-polymer may be added to the vertebral bodies to replace damaged tissue and facilitate the vertebral bodies with rolling over the gel. In other instances, a more rigid version of S-polymer may be used for the gel itself. S-polymer may be used to replace the gel.

Each disc works in concert with two facet joints forming a spinal motion segment. Through time the facet joints may ware down. In some instances, a more rigid version of S-polymer may be cast in a mold modeled after the facet joints. After curing, a less rigid version of S-polymer may be added to the S-polymer facet joints to either fully or partially replace a patient's portion of the spine. The biomechanical function of each pair of facet joints is to guide and limit the movement of the spinal motion segment. The surfaces of the joint are coated with cartilage that helps each joint move smoothly directly behind the discs. S-polymer may be added to the cartilage to replace the cartilage as the bodies natural cartilage wears down over time.

The ring-like vertebral bodies create a vertical tunnel called the spinal canal or neural canal. The spinal cord and spinal nerves pass through the spinal canal which protects them from injury. S-polymer may be used to fill in portions of vertebral bodies that have been damaged over time to further protect the spinal nerves. The spinal cord is the major column of nerve tissue that is connected to the brain and serves as an information superhighway between the brain and the body. A problem with polymers that rely on metal and that are not silicon based is that they contain substances damaging to nerve tissue. Therefore, the use of these polymers is not favorable because though they may treat human bone, the presence of chemicals toxic to nerves may harm a patient.

The nerves in the spinal cord branch off to form pairs of nerve roots that travel through the small openings between the vertebrae. During disc herniation, the disc degenerates and breaks down and the inner core can leak out through the outer portion of the disc. S-polymer may be used in several ways to treat this. First, S-polymer may be used on the disc itself. The application of S-polymer to an exposed disc may strengthen the disc and prevent or slow down further degeneration. Second, if a disc has already deteriorated, S-polymer may be added to take most of the friction rather than have the disc be ground down more.

Disc herniation may put direct pressure on the nerve. S-polymer may be added to the nerve to prevent the disc from harming or causing the nerve to fire neurological signals. These signals are often associated with pain and thus S-polymer may be applied as a form of pain management. Lumbar herniated disc symptoms include low back pain, pain in the legs and buttocks, leg numbness and tingling. S-polymer may be used to treat these symptoms.

Endoscopic lumbar discectomy supplemented with S-polymer is a minimally invasive procedure often used for treating lumbar herniated discs. S-polymer may be used in an endoscopic lumbar discectomy. First a thin guide wire is placed under x-ray control down to the involved level of the spine. A tapered dilator may be inserted over the guide wire and a small tube is inserted over the dilator to create a portal to the herniated disc. The endoscope is then placed through the tube and the discectomy is performed using special instruments. After the removal of the damaged portion of the herniated disc, the surgeon may add an effective amount of S-polymer to the damaged region. The S-polymer fills in the portion of the disc removed which may restore normal function to a patient. S-polymer may also be added to relieve nerve root compression.

Spinal fusion may be performed on the spine with S-polymer. Two or more vertebrae may be fused together using surgical hardware and bone graft material, or S-polymer. The spine consists of a series of interconnected bones called vertebrae extending from the base of the skull to the tailbone. Each vertebra connects with a vertebra above and below at the facet joints allowing them to move relative to one another. In between each bony vertebra lies a shock absorbing intervertebral disc. The facet joints and intervertebral discs work together to permit the bending and twisting motions of the back and neck. Protected within the vertebral column is the spinal cord which connects the brain to the rest of the body. Spinal nerves emanate from the spinal cord at regular intervals.

Spinal fusions may be used to treat the following conditions a fractured vertebra excessive motion between vertebrae causing instability and spondylosis a degenerative arthritis condition that may cause loss of normal spinal structure and function and spondylolisthesis a condition in which one vertebra slips forward relative to the one next to it other conditions that may require surgery include osteoarthritis of the facet joints a spinal deformity such as scoliosis or kyphosis or a bulging or herniated disc which can press on the exiting spinal nerve.

Spinal fusion is traditionally designed to eliminate movement between the affected vertebrae making the spine more stable and decreasing pain. However, a major drawback of spinal fusions is the vertebrae may be more brittle after surgery and movement is hindered. The application of S-polymer makes the fused vertebrae less brittle because the introduction of S-polymer makes the overall structure more bendable and less inclined to break. Additionally though fused, the vertebrae may actually bend and move due to S-polymer's unique characteristics. Thus even though the vertebrae are thought to be fused in a traditional surgical sense, there is actually some movement allowed between them.

In some spinal fusions the patient is on its stomach and a surgeon will make an incision directly over the spine. If a patient is having surgery on the cervical spine in the neck the surgeon may approach this area from the front. In some cases, a spinal fusion may be performed using a newer less invasive laparoscopic technique rather than one or two large incisions. A laparoscopic spinal fusion requires several tiny keyhole incisions through which the laparoscope and special surgical instruments are inserted. These instruments may be loaded with S-polymer and used to administer the polymer to a part of the spine. Using a high-speed drill and other instruments a surgeon will remove the disc between the two vertebral bodies to be fused. In other instances, a surgeon may simply apply an effective amount of S-polymer to the damaged site, thus fixing the disc and vertebrae. Next the surgeon will insert the bone graft, S-polymer, or a bone graft S-polymer matrix into the space between these two vertebrae. The surgeon may also place a plate and screws over the graft to hold the vertebrae together until they fuse into one bone. To complete the procedure the surgeon will close the deep tissue and skin incision with stitches. Many surgeons may also place drains beneath the skin that will remain in place for a few days after the procedure. Unlike other spinal materials, S-polymer does not cause more drainage to occur.

Anterior cervical discectomy and fusion may also be performed with S-polymer. Degenerative diseases of the cervical intervertebral discs can cause spinal stenosis. Protruding discs tissue can put pressure on the nerves that travel through the spine which can lead to serious consequences including pain and nerve damage. The application of S-polymer around nerves can prevent this pressure and strengthen intervertebral discs. During anterior cervical dissection a thorough discectomy is performed first to completely eject the problem disc and release the spinal cord. S-polymer may be added to the ejection site or added around nerves to prevent inflammation and nerve damage. Vertebral end plates are then prepared to ensure placement of the implant. In some instances, S-polymer may be used as a replacement of vertebral end plates. A vascularized surface for stimulating fusion may be placed in the cavity between the vertebrae to select the correct implant size. Then a suitable size implant is inserted with the holder. The central space of the implant is preloaded with a graft. This graft may contain a portion of S-polymer, and in some instances the graft can be entirely S-polymer. Two curved anchoring plates are inserted through the interior of the holder and implant self-retaining plates are immersed in the vertebral bodies and securely fix the implant with the vertebrae. To provide the stability needed for successful fusion the implant maintains the spacing of the vertebrae while the fusion takes place. After the fusion is completed a solid bone mass supplemented with S-polymer forms and two vertebrae are joined together Anterior Cervical Corpectomy may also be performed with S-polymer. A corpectomy is one approach to curing ailments of the anterior cervical spine. One version of Cervical Corpectomy is to do an anterior cervical discectomy in fusion. Sometimes when there are two levels involved and the compression is more severe and more extensive, decompression is required which may necessitate a corpectomy or removal of the vertebral body. Neck pain and complaints of pain and numbness radiating into the upper extremities with one side being worse than the other are common. An MRI scan of the cervical spine may show compression at C4 and C5. Measurements of the compression from an MRI or other imaging scan may be used to determine a therapeutically effective amount of S-polymer. In the axial cut there may be significant compression of the spinal cord and there may be signal change within the spinal cord indicative of ongoing myopathy. A C5 corpectomy with C4 the C6 inter body fusion is also common.

An incision on a side of the patient's neck section may be carried down to the anterior cervical spine. A marker may be placed at the appropriate level. S-polymer impregnated with a marker may also be used as the marker itself. Incising the disc with a knife may allow defective disc material to be removed and an amount of S-polymer to be applied. Additionally, tools may be used to burn off anterior osteophytes. In other instances, S-polymer may be applied to where the osteophytes were burned off. Osteophytes may also be added to S-polymer to facilitate bone growth and attachment of the S-polymer to bone or ligament. Drilling into the disc space to further develop the disc space at the level above the bone may also be appropriate. Shavings may be collected for bone grafting and may also be applied to S-polymer.

Cervical decompression with S-polymer is another effective means of treating spinal trauma. Decompression and fusion of the anterior cervical spine is another method of alleviating spinal injuries. Decompression and fusion of the anterior cervical spine may be accomplished from one level or multiple levels. The bony vertebra the intervertebral disc and the spinal cord are the main anatomical parts involved in Cervical decompression. The application of S-polymer to any of these parts may aid in surgery and recover. Compression on any of these anatomical parts caused by trauma, age, or other forces may cause pain numbness and weakness. Decompression may be performed to relieve pressure placed on the nerve roots and the spinal cord. S-polymer may be added to areas of trauma to further aid in decompression. During the surgical procedure, the spine may be stabilized with a bone graft, the bone graft may contain S-polymer or not, and a plate fixation. The patient may also require multi-level decompression and fixation with a bone graft and plate. S-polymer may be added to all levels or only a select few levels during the procedure.

Cervical laminoplasty with S-polymer is also another effective treatment of spinal trauma. Some patients have a condition in their neck that puts pressure on the spinal cord or spinal nerves. A doctor may recommend a cervical laminoplasty. The portion of spine in the neck also called the cervical spine has seven bones called vertebrae. The front part of each vertebra is called the vertebral body except for the first vertebra. Between most vertebrae is a soft cushion of cartilage called an intervertebral disc. These discs may be entirely replaced with S-polymer, or partially supplemented with S-polymer. The back part of each vertebra has a curved section called the vertebral arch. Over time, the vertebral arch may wear down or be damaged due to trauma. The addition of S-polymer to the vertebral arch may aid in healing. Except for the first vertebra each vertebral arch has a bony projection called the spinous process on each side of the spinous process is a flat piece of bone called a lamina. The vertebral arch of the vertebra surrounds and protects the spinal cord. A column of nervous tissue connecting the brain to other nerves in the body to the spinal cord passes through an enclosed space called the vertebral canal which is formed by the vertebral arches of the vertebrae. Over time the cervical spine may develop problems such as a bulging disc or bony growths on the vertebrae called bone spurs. These changes can narrow a patient's vertebral canal and put pressure on the spinal cord or the nerves that branch off of it. The pressure may cause neck pain and stiffness or pain numbness and weakness in the arms or hands. Before a spinal procedure an intravenous line or IV may be started or a patient may be given antibiotics through the IV to decrease the chance of infection. Patients may be given general anesthesia to make them unconscious and not feel pain. During the procedure a breathing tube will be inserted through the mouth and down the patient's throat. A surgeon will make an incision on the back of the patient's neck. The laminae of the affected vertebrae will be exposed, and the surgeon will remove the outer layer of bone from each lamina forming two troughs. If the surgeon uses the open door technique the surgeon will cut the rest of the way through one of the troughs and pull open the vertebral arch using the other trough as a hinge. This relieves the pressure on the spinal cord. If the surgeon uses the French door or double door variation of this technique both troughs will be used as hinges. This will allow the surgeon to split the spinous process and open the vertebral arch in the middle. Usually, the vertebral arch will be opened on more than one a patient's cervical vertebrae. Bone graft material, bone graft with S-polymer, or only S-polymer along with metal plates attached to it may be inserted into each vertebral arch. To hold the opening open, a surgeon will close a patient's incision with sutures. Surgical skin glue, S-polymer, or staples may be used to close the neck, and the neck will be placed in a collar to keep it still while bones heal. After the procedure a patient's breathing tube will be removed and the patient will be taken to the recovery area for monitoring. Patients may be given pain medication as needed. A patient will wear a neck collar for several weeks. The patient may be released from the hospital within two to three day safter the procedure.

Cervical disc arthroplasty or cervical disc replacement may also be administered with S-polymer and is gaining popularity in the United States for several reasons. First insurance companies are realizing that it has a better cost benefit ratio for younger patients than an anterior cervical discharging infusion. When S-polymer is used for the procedure, especially with younger patients, the need for surgeries later in life is greatly reduced because when S-polymer fuses to the bone, it makes the overall structure more secure and flexible, resulting in less surgery later on in life. Second, the FDA has approved this procedure for two level surgery. Additionally, when S-polymer is used as a disc replacement it has a higher success rate than other fusion replacements. Cervical disc replacements with S-polymer is more advantages than regular disc replacement is because S-polymer not only makes the disc more structurally sound, but prevents nerves from being damaged by changes to the spine that occur during and after surgery. When S-polymer is used around the nerve instead of putting a spacer and a plate on the spine, surgeons or trauma specialists may apply an effective amount of S-polymer to solve the entire problem.

S-polymer may also be used to aid in thoracic laminectomy. A narrowing of the spinal canal may cause painful pressure on the spinal cord or nerves. Sometimes the source of this narrowing is a tumor that has spread to the thoracic region of the spine and is pushing on the spinal cord. A thoracic laminectomy removes the lamina from vertebral bodies, replacing it with S-polymer, and providing access to remove the tumor and eliminate pressure on the spinal cord. After removing bone, instrumentation may also be added to stabilize the vertebrae. In other instances, the addition of S-polymer instead of instrumentation may lead to a fuller recovery and more movement in the patient. An incision may be made along the middle of the backbone. The spine is exposed, and surgical instruments are used to remove the spinous processes. The lamina portions of a vertebrae are then removed providing access to the tumor. Surgical instruments are used to remove the tumor removing both the tumor and overlying bone that pushes into the spinal cord relieves the compression. S-polymer may be introduced to support the spine. Holes are made in the pedicle of intact vertebrae and screws are placed in. In other instances, screws may be infused with S-polymer or S-polymer alone may be introduced to the site. Next rods are positioned between the screws (or S-polymer complex which is a combination of screw and S-polymer, or S-polymer alone) and fastened in place. The rod and screw instrumentation provides stability to the spine. The incision is closed and dressed to complete the surgery. Radiation treatments are frequently used two to four weeks after surgery to treat any tumor remaining in the spine. Adding the instrumentation or more S-polymer after the laminectomy increases the strength of the spine and may decrease the need for a post-operative brace. Patients should avoid heavy lifting bending twisting and turning for six to twelve weeks post-surgery.

S-polymer may also be used in a posterior lumbar fusion. The purpose of the posterior lumbar fusion surgery is to fuse two or more vertebral bones of the lower back into one. This result is achieved by tricking the body into thinking the individual vertebral bones are broken at which point your body attempts to heal this break into one bone. This healing can also be facilitated with S-polymer. By adding S-polymer to the broken portion of the bones, the bones become more structurally stable, and the body takes less time to heal. The procedure begins with a surgeon making an incision along the midline of a patient's lower back. The back muscles are gently moved to the side so the spine is visible. Usually, a fusion is performed together with the laminectomy procedure to removes bone pressure on the nerve. Fusion can be necessary after removal of stabilizing bony anatomy. To solve complaints related to fractures herniations infections or tumors for the inner body fusion the facet joint may be removed. To expose and ensure the removal of the disc a surgeon may move the spinal nerves to the side and replace the disc with a bone graft or an interbody fusion device, or S-polymer. Care is taken to protect the nerve sac during insertion of the interbody fusion cages or graft or S-polymer. The additional space around the cage is then backed with bone material and/or S-polymer. To support the healing process the spine must be stabilized for a proper fusion to occur. A combination of screws, rods, and S-polymer are used to achieve the stabilization of the spine. The screws can be placed in the pedicles which are the strongest part of the spine. Rods, bolts, and S-polymer are then used to fashion and link the screws to one another. Additional bone graft and S-polymer may be placed along the sides of the vertebral bones. Posterior lumbar fusion generally takes two to five hours. Traditionally patients were admitted to the hospital for a few days, but minimally invasive techniques now allow many to return home the same day of the operation. Patients can expect a return to normal physical activities in three to six months S-polymer may also be used with Lumbar Stenosis Decompression. An estimated 1.5 million patients visit doctor's offices each year for lumbar stenosis decompression. It is also one of the most common reasons for spine surgery. Decompression for stenosis with traditional rigid instruments presents a unique challenge for physicians and patients. Though the procedure may remove pain and allow normal use of the spine, the use of rigid materials, metals, screws and bone graft may leave a patient more rigid than before. The use of S-polymer during this procedure may increase flexibility in a patient's post-surgery. Removal of part or all of the facet joint is required to access and decompress impinging tissue in the lateral recess and foramen. However, this removal can lead to spinal instability and accelerated disc degeneration. The addition of S-polymer to the aforementioned regions may reduce disc degeneration. S-polymer may provide decompression from the inside out. S-polymer may act as a direct decompression system that aims to preserve facet joint integrity while helping to minimize muscle trauma without an implant. S-polymer may accommodate both open and tube based approaches to surgery and can be used ipsilaterally and contralaterally to decompress up to four nerve roots from a single point incision. Precision decompression using S-polymer may be accomplished via three steps access, confirmation and decompression. During the access phase an interlaminar window is created and a probe or other tool may be inserted and deployed out to the foramen. A guidewire may be passed through the probe or tool and advanced until it exits the skin where it is captured in the distal handle. The probe is then removed. A neuro sensor device may then be attached to the guidewire and pulled into the foramen. Following confirmation, the neuro sensor device is removed, and S-polymer injected into the site. A micro blade shaver device may be pulled across the target tissue and into the foramen.

Lumbar microdiscectomy with S-polymer may be used as a minimally invasive procedure used to relieve pain and weakness caused by a herniated or ruptured discs. The herniated disc presses against nerve roots which causes shooting pain down one or both legs often referred to as sciatica. Using fluoroscopy and/or a special type of x-ray the level of the injured disc is located along the spine. A small incision less than an inch may be made on the patient's lower back directly over the disc space to access the disc. At this point an amount of S-polymer may be added to the incision and the patient sealed up to end the procedure. During other versions of the procedure, a set of tubular dilators may be passed down to the spine splitting the overlying muscles. The use of S-polymer allows the surgeon excellent access to the spine with less disruption of muscle tissue resulting in less pain post-surgery and a quicker recovery than traditional open surgery. Once the spine is exposed a tiny amount of the lamina the bone structure that protects the spinal nerve roots may be removed to create a window for the passage of surgical instruments. This passage is referred to as the laminotomy. S-polymer may be added here to improve flexibility and aid in recovery. A microscope may be brought in to magnify the surgical field. The pinched nerve root may be gently retracted to allow access to the injured disc. At other times it may be favorable to add S-polymer to the wound site to repair both the injured disc and ease pressure on the pinched nerve. Using micro instruments, the damaged portion of the disc is removed while the healthy portion is left intact and functions to cushion the vertebra. Partial disc removal or discectomy is a necessary procedure to alleviate nerve compression and return the nerve root to a healthy position the small wound is closed with absorbable sutures and a tiny dressing applied at the spine.

S-polymer may also be used with posterior lumbar interbody fusion. The purpose of the surgery is to fuse two or more vertebral bones of a patient's lower back to one. This is achieved by tricking the body into thinking the individual vertebral bones are broken at which point your body attempts to heal the break into one bone. The procedure begins with a surgeon making an incision along the midline of the patient's lower back. The back muscles are gently moved to the side so the spine is visible. Usually, a fusion is performed together with the laminectomy procedure. Laminectomy removes boney pressure on the nerve sac. Fusion can be necessary after removal of stabilizing bone anatomy to solve complaints related to fractures, herniations, infections, or tumors. For the interbody fusion, the facet joint may be removed to expose and ensure the removal of the disc. The surgeon moves the spinal nerves to the side and replaces the disc with a bone graft or an interbody fusion device. Care is taken to protect the nerve sac during insertion of the interbody fusion cages or graft. The additional space around the cage is then backed with bone material to support the healing process. The spine must be stabilized for a proper fusion to occur. A combination of screws and rods are used to achieve this stabilization of the spine. The screws can be placed in the pedicles, which are the strongest part of the spine. Rods and bolts are then used to fasten and link the screws to one another. Additional bone graft is placed along the sides of the vertebral bones. Posterior lumbar fusion generally runs from two to five hours. Traditionally, patients were admitted to the hospital for a few days, but minimally invasive techniques now allow many to return home the same day of the operation. Patients can expect to return to normal physical activities 3 to 6 months but a decision on specific time should be left to the surgeon.

The spine also called the backbone or vertebral column is composed of 33 Bones called vertebrae which provide your body with support and protect your spinal cord from injury the vertebrae can be divided into five groups cervical, thoracic, lumbar, sacral, and the coccyx each of which has unique features suited to their functions. There are seven cervical vertebrae numbered C1 to C7. The thoracic vertebrae are numbered T1 to T12. The 5 lumbar vertebrae numbered are L1 to L5. The sacral vertebrae numbered S1 to S5, and the coccyx. The application of S-polymer to all of these vertebrae is appropriate. The upper 24 vertebrae are separated by intervertebral discs the sacral vertebrae and the bones of the coccyx are fused. The cervical vertebrae which are the vertebrae of your neck support your head which weighs around 10 to 13 pounds. C1and C2 are specialized vertebrae that allow for the greatest range of motion of all the vertebrae. C1 is called Atlas after the man from Greek mythology who held up the earth it is ring shaped and attaches directly to your skull. The addition of S-polymer here can help in the fusion of the C1 to the head. This vertebra allows you to nod your head while serving as an axis which C1 pivots allowing you to shake your head when saying no. C1 is able to pivot on this vertebra thanks to a specialized process called the dens or odontoid process. When this part of the vertebrae is damaged the addition of S-polymer can restore function. The thoracic vertebrae which are the vertebrae of your mid and upper back hold the ribcage and protect your heart and lungs. These vertebrae have a limited range of motion. They also form a complex with muscles, S-polymer may be added to this complex in the event of trauma.

The lumbar vertebrae which are the vertebra of the lower back bear the weight of the upper body and are larger in order to support stress especially when lifting something heavy. The sacral vertebrae connect the spine to the hip bones. These vertebrae are fused together with the hip bones and form the pelvic girdle. The coccyx or tailbone is made up of four fused bones which provide attachment points for ligaments and muscles of the pelvic floor.

The vertebra have three parts the body, vertebral arch, and the processes. The addition of S-polymer to any of these three parts may increase structural integrity of the vertebrae. The body bears weight while the vertebral arch houses the spinal cord, and the processes allow for muscle attachment. The arch may be supplemented with S-polymer to allow for better linkage between the vertebrae and attached muscle. During trauma, sometimes muscle may be ripped away from the vertebral arch which may require adhesion back to the bone. S-polymer may be used to facilitate this adhesion. The vertebral arch is further organized into two supporting pedicles and two laminae. The space inside which houses the spinal cord is called the vertebral foramen. Under each pedicle spinal nerves exit and pass through the intervertebral foramina. Seven bony processes arise from each vertebral arch to form facet joints and processes for muscle attachment. Facet joints allow for back motion. Each vertebra has two pairs of facet joints one pair connects to the vertebra above and one pair that connects to the vertebra below there is also a pair of transverse processes and a spinous process. Between the vertebra are the intervertebral discs which provide cushioning and prevent the bones from rubbing together. Note that there is no intervertebral disc between C1 and C2. However, S-polymer may be added between C1 and C2 to increase structural integrity of the spine. Discs are composed of an annulus which is made up of several layers or lamina of fibrocartilage criss-crossing fibrous bands that attach between the bodies of the vertebrae above and below and a gel filled center called the nucleus. The nucleus distributes the pressure evenly within each disc.

During compression the nucleus is full of proteoglycans large molecules with sugar subunits that are very hydrophilic. This structure swells with water unless it experiences constraints from the surrounding tissues hence the nucleus absorbs fluid at night or when you are lying down and then this fluid is pushed out during the day when you are upright, and pressure is applied to the intervertebral discs. One reason it is believed humans shorten as they age is because the discs lose the ability to reabsorb fluid as they age. The discs flatten and become more brittle. Replacing or supplementing these discs with S-polymer can prevent shortening or damage.

One possible method for performing a medical procedure could include a method of performing a medical procedure on a spine using S-polymer comprising: identifying compression or trauma between or on the vertebrae of a patient's spine; sedating a patient and placing the patient on the patient's stomach so the patient's vertebrae is exposed to a surgeon; making at least one incision on a patient's back or neck; using a drill to remove at least a portion of a disc between two vertebral bodies and at least a portion of a vertebral body; injecting a solution containing S-polymer between the two vertebral bodies; waiting at least 30 seconds for the S-polymer to harden. The above method could be used wherein the patient suffers from a fractured vertebra, excessive motion between vertebrae, instability of the spine or bones, spondylosis, arthritis, spondylolisthesis, osteoarthritis of the facet joints, scoliosis, kyphosis, bulging of a herniated disc, spinal trauma. The above method could also be used wherein S-polymer is mixed with a portion of bone graft. The above method could also be used wherein the medical procedure is a spinal fusion. The above method could also be used wherein the S-polymer injected between the vertebral bodies is infused into a spongy portion of tissue within a vertebra.

The above method could also be used wherein the S-polymer comprises a silicone mixture, and wherein the silicone mixture comprises (a) a vinyl end-blocked polydimethylsiloxane as a first silicone elastomer component and a platinum catalyst, and (b) a vinyl end-blocked polydimethylsiloxane as a second silicone elastomer component and a trimethyl end-blocked methyl-hydrogen siloxane polymer as a silicone crosslinker; and (c) wherein the polymerizable composition comprises a first and a second adhesion promoter that synergistically enhance adhesion of the polymerized composition to the skin, and wherein the first and second adhesion promoter are N-(triethoxysilylpropyl)-O-polyethylene oxide urethane and tetrapropoxysilane.

Another method of performing spinal surgery with S-polymer could be described as a method of performing a medical procedure including a spinal fusion on a spine of a patient suffering from fractured vertebra, excessive motion between vertebrae, instability of the spine or bones, spondylosis, arthritis, spondylolisthesis, osteoarthritis of the facet joints, scoliosis, kyphosis, bulging of a herniated disc, spinal trauma, using S-polymer wherein the S-polymer is mixed with a portion of bone graft, wherein the S-polymer further contains a silicone mixture, and wherein the silicone mixture comprises (a) a vinyl end-blocked polydimethylsiloxane as a first silicone elastomer component and a platinum catalyst, and (b) a vinyl end-blocked polydimethylsiloxane as a second silicone elastomer component and a trimethyl end-blocked methyl-hydrogen siloxane polymer as a silicone crosslinker; and (c) wherein the polymerizable composition comprises a first and a second adhesion promoter that synergistically enhance adhesion of the polymerized composition to the skin, and wherein the first and second adhesion promoter are N-(triethoxysilylpropyl)-O-polyethylene oxide urethane and tetrapropoxysilane comprising: identifying compression or trauma between or on the vertebrae of a patient's spine; sedating a patient and placing the patient on the patient's stomach so the patient's vertebrae is exposed to a surgeon; making at least one incision on a patient's back or neck; using a drill to remove at least a portion of a disc between two vertebral bodies and at least a portion of a vertebral body; injecting a solution containing S-polymer between the two vertebral bodies, wherein the S-polymer injected between the vertebral bodies is infused into a spongy portion of tissue within a vertebra; waiting at least 30 seconds for the S-polymer to harden.

Another method of treating spinal trauma could be described as A method of treating spinal trauma comprising: identifying at least a portion of a vertebrae of a patient including a vertebral body, an intervertebral disc, a vertebral arch, a spinous process, a lamina, a vertebral canal, a bone spur that is damaged due to trauma; making an incision on a patient that exposes the portion of a damaged vertebrae; applying a therapeutically effective amount of S-polymer to the portion of damaged vertebrae; waiting at least 30 seconds for the S-polymer to cure.

Another method of treating spinal trauma could be described as a method of treating spinal trauma comprising: identifying at least a portion of a vertebrae of a patient including a vertebral body, an intervertebral disc, a vertebral arch, a spinous process, a lamina, a vertebral canal, a bone spur that is damaged due to trauma; making an incision on a patient that exposes the portion of a damaged vertebrae; applying a therapeutically effective amount of S-polymer wherein the S-polymer comprises a silicone mixture, and wherein the silicone mixture comprises (a) a vinyl end-blocked polydimethylsiloxane as a first silicone elastomer component and a platinum catalyst, and (b) a vinyl end-blocked polydimethylsiloxane as a second silicone elastomer component and a trimethyl end-blocked methyl-hydrogen siloxane polymer as a silicone crosslinker; and (c) wherein the polymerizable composition comprises a first and a second adhesion promoter that synergistically enhance adhesion of the polymerized composition to the skin, and wherein the first and second adhesion promoter are N-(triethoxysilylpropyl)-O-polyethylene oxide urethane and tetrapropoxysilane.

Another method could be described as a method of treating spinal trauma comprising: identifying at least a portion of a vertebrae of a patient including a vertebral body, an intervertebral disc, a vertebral arch, a spinous process, a lamina, a vertebral canal, a bone spur that is damaged due to trauma; making an incision on a patient that exposes the portion of a damaged vertebrae; applying a therapeutically effective amount of S-polymer to the portion of damaged vertebrae; waiting at least 30 seconds for the S-polymer to cure.

Another method could be described as a method of treating spinal trauma comprising: identifying at least a portion of a vertebrae of a patient including a vertebral body, an intervertebral disc, a vertebral arch, a spinous process, a lamina, a vertebral canal, a bone spur that is damaged due to trauma; making an incision on a patient that exposes the portion of a damaged vertebrae, at least a portion of a vertebrae of a patient is drilled and removed before the application of a therapeutically effective amount of S-polymer wherein the S-polymer introduced to the portion of damaged vertebrae is infused into a spongy portion of tissue on a vertebra; applying a therapeutically effective amount of S-polymer wherein the S-polymer is mixed with a portion of bone graft to the portion of damaged vertebrae; waiting at least 30 seconds for the S-polymer to cure.

Another method could be described as a method of treating spinal trauma comprising performing a thoracic laminectomy on a patient, and the patient's lamina is removed and replaced with S-polymer, identifying at least a portion of a vertebrae of a patient including a vertebral body, an intervertebral disc, a vertebral arch, a spinous process, a lamina, a vertebral canal, a bone spur that is damaged due to trauma; making an incision on a patient that exposes the portion of a damaged vertebrae, at least a portion of a vertebrae of a patient is drilled and removed before the application of a therapeutically effective amount of S-polymer wherein the S-polymer introduced to the portion of damaged vertebrae is infused into a spongy portion of tissue on a vertebra; applying a therapeutically effective amount of S-polymer wherein the S-polymer is mixed with a portion of bone graft to the portion of damaged vertebrae; waiting at least 30 seconds for the S-polymer to cure.

Another method could be described as a method of treating spinal trauma wherein the spinal trauma is selected from a group consisting of fractured vertebra, excessive motion between vertebrae, instability of the spine or bones, spondylosis, arthritis, spondylolisthesis, osteoarthritis of the facet joints, scoliosis, kyphosis, bulging of a herniated disc, spinal trauma. comprising performing a thoracic laminectomy on a patient, and the patient's lamina is removed and replaced with S-polymer, identifying at least a portion of a vertebrae of a patient including a vertebral body, an intervertebral disc, a vertebral arch, a spinous process, a lamina, a vertebral canal, a bone spur that is damaged due to trauma; making an incision on a patient that exposes the portion of a damaged vertebrae, at least a portion of a vertebrae of a patient is drilled and removed before the application of a therapeutically effective amount of S-polymer wherein the S-polymer introduced to the portion of damaged vertebrae is infused into a spongy portion of tissue on a vertebra; applying a therapeutically effective amount of S-polymer wherein the S-polymer is mixed with a portion of bone graft to the portion of damaged vertebrae; waiting at least 30 seconds for the S-polymer to cure.

Another method of treating spinal trauma could be described as a method of performing endoscopic lumbar discectomy with an S-polymer comprising: placing a thin guide wire under mechanical control down to the involved level of an injured spine; inserting a tapered dilator over the guide wire and inserting a small tube over the dilator to create a portal to a damaged area of the spine; placing an endoscope through the tube and performing a discectomy on the damaged part of the spine; removing at least a piece of damaged spine; injecting an effective amount of S-polymer to the damaged part of the spine.

Another method of treating spinal trauma could be described as a method of performing endoscopic lumbar discectomy with an S-polymer comprising: placing a thin guide wire under mechanical control down to the involved level of an injured spine, wherein the piece of damaged spine consists of at least a portion of a vertebral body, an intervertebral disc, a vertebral arch, a spinous process, a lamina, a vertebral canal, a bone spur, a tumor, spongy tissue, calcium containing tissue; inserting a tapered dilator over the guide wire and inserting a small tube over the dilator to create a portal to a damaged area of the spine; placing an endoscope through the tube and performing a discectomy on the damaged part of the spine; removing at least a piece of damaged spine; injecting an effective amount of S-polymer, wherein the S-polymer is mixed with a portion of bone graft, to the damaged part of the spine, wherein the addition of S-polymer removes nerve root compression and wherein the S-polymer is infused into a spongy portion of tissue.

Another method of treating spinal trauma could be described as a method of performing endoscopic lumbar discectomy with an S-polymer comprising: placing a thin guide wire under mechanical control down to the involved level of an injured spine, wherein the piece of damaged spine consists of at least a portion of a vertebral body, an intervertebral disc, a vertebral arch, a spinous process, a lamina, a vertebral canal, a bone spur, a tumor, spongy tissue, calcium containing tissue; inserting a tapered dilator over the guide wire and inserting a small tube over the dilator to create a portal to a damaged area of the spine; placing an endoscope through the tube and performing a discectomy on the damaged part of the spine; removing at least a piece of damaged spine; injecting an effective amount of S-polymer, wherein the S-polymer wherein the S-polymer comprises a silicone mixture, and wherein the silicone mixture comprises (a) a vinyl end-blocked polydimethylsiloxane as a first silicone elastomer component and a platinum catalyst, and (b) a vinyl end-blocked polydimethylsiloxane as a second silicone elastomer component and a trimethyl end-blocked methyl-hydrogen siloxane polymer as a silicone crosslinker; and (c) wherein the polymerizable composition comprises a first and a second adhesion promoter that synergistically enhance adhesion of the polymerized composition to the skin, and wherein the first and second adhesion promoter are N-(triethoxysilylpropyl)-O-polyethylene oxide urethane and tetrapropoxysilane, to the damaged part of the spine, wherein the addition of S-polymer removes nerve root compression.

Closing Comments

Throughout this description, the embodiments and examples shown should be considered as exemplars, rather than limitations on the apparatus and procedures disclosed or claimed. Although many of the examples presented herein involve specific combinations of method acts or system elements, it should be understood that those acts and those elements may be combined in other ways to accomplish the same objectives. With regard to flowcharts, additional and fewer steps may be taken, and the steps as shown may be combined or further refined to achieve the methods described herein. Acts, elements and features discussed only in connection with one embodiment are not intended to be excluded from a similar role in other embodiments.

As used herein, "plurality" means two or more. As used herein, a "set" of items may include one or more of such items. As used herein, whether in the written description or the claims, the terms "comprising", "including", "carrying", "having", "containing", "involving", and the like are to be understood to be open-ended, i.e., to mean including but not limited to. Only the transitional phrases "consisting of" and "consisting essentially of", respectively, are closed or semi-closed transitional phrases with respect to claims. Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. As used herein, "and/or" means that the listed items are alternatives, but the alternatives also include any combination of the listed items.

It is claimed:

1. A method of performing a medical procedure on a spine with a fractured vertebra using S-polymer comprising:

identifying compression or trauma between or on the vertebrae of a patient's spine;

sedating a patient and placing the patient on the patient's stomach so the patient's vertebrae is exposed to a surgeon;

making at least one incision on a patient's back or neck;

using a drill to remove at least a portion of a disc between two vertebral bodies and at least a portion of a vertebral body;

injecting a solution containing S-polymer, the S-polymer comprising a silicone mixture, and wherein the silicone mixture comprises (a) a vinyl end-blocked polydimethylsiloxane as a first silicone elastomer component and a platinum catalyst, and (b) a vinyl end-blocked polydimethylsiloxane as a second silicone elastomer component and a trimethyl end-blocked methyl-hydrogen siloxane polymer as a silicone crosslinker; and (c) wherein the polymerizable composition comprises a first and a second adhesion promoter that synergistically enhance adhesion of the polymerized composition to the skin, and wherein the first and second adhesion promoter are N-(triethoxysilylpropyl)-O-polyethylene oxide urethane and tetrapropoxysilane, between the two vertebral bodies;

waiting at least 30 seconds for the S-polymer to harden.

2. The method of claim 1 wherein the S-polymer is mixed with a portion of bone graft.

3. The method of claim 1 wherein the medical procedure is a spinal fusion.

4. The method of claim 1 wherein the S-polymer injected between the vertebral bodies is infused into a spongy portion of tissue within a vertebra.

5. A method of treating spinal trauma comprising:

identifying at least a portion of a vertebrae of a patient that is damaged due to trauma including the portion being at least one of the following: a vertebral body, an intervertebral disc, a vertebral arch, a spinous process, a lamina, a vertebral canal, or a bone spur that is damaged due to trauma;

making an incision on a patient that exposes the portion of a damaged vertebrae;

applying a therapeutically effective amount of S-polymer, the S-polymer comprising a silicone mixture, and wherein the silicone mixture comprises (a) a vinyl end-blocked polydimethylsiloxane as a first silicone elastomer component and a platinum catalyst, and (b) a vinyl end-blocked polydimethylsiloxane as a second silicone elastomer component and a trimethyl end-blocked methyl-hydrogen siloxane polymer as a silicone crosslinker; and (c) wherein the polymerizable composition comprises a first and a second adhesion promoter that synergistically enhance adhesion of the polymerized composition to the skin, and wherein the first and second adhesion promoter are N-(triethoxysilylpropyl)-O-polyethylene oxide urethane and tetrapropoxysilane, to the portion of damaged vertebrae;

waiting at least 30 seconds for the S-polymer to cure.

6. The method of claim 5 wherein the S-polymer is mixed with a portion of bone graft.

7. The method of claim 5 wherein the S-polymer introduced to the portion of damaged vertebrae is infused into a spongy portion of tissue on a vertebra.

8. The method of claim 5 wherein at least a portion of a vertebrae of a patient is drilled and removed before the application of a therapeutically effective amount of S-polymer.

9. The method of claim 5 wherein a thoracic laminectomy is performed on a patient, and the patient's lamina is removed and replaced with S-polymer.

10. A method of performing endoscopic lumbar discectomy with an S-polymer comprising:

placing a thin guide wire under mechanical control down to the involved level of an injured spine;

inserting a tapered dilator over the guide wire and inserting a small tube over the dilator to create a portal to a damaged area of the spine;

placing an endoscope through the tube and performing a discectomy on the damaged part of the spine;

injecting an effective amount of S-polymer the S-polymer comprising a silicone mixture, and wherein the silicone mixture comprises (a) a vinyl end-blocked polydimethylsiloxane as a first silicone elastomer component and a platinum catalyst, and (b) a vinyl end-blocked polydimethylsiloxane as a second silicone elastomer component and a trimethyl end-blocked methyl-hydrogen siloxane polymer as a silicone crosslinker; and (c) wherein the polymerizable composition comprises a first and a second adhesion promoter that synergistically enhance adhesion of the polymerized composition to the skin, and wherein the first and second adhesion promoter are N-(triethoxysilylpropyl)-O-polyethylene oxide urethane and tetrapropoxysilane to the damaged part of the spine.

11. The method of claim 10 wherein the addition of S-polymer removes nerve root compression.

12. The method of claim 10 wherein the piece of damaged spine consists of at least a portion of a vertebral body, an intervertebral disc, a vertebral arch, a spinous process, a lamina, a vertebral canal, a bone spur, a tumor, spongy tissue, or calcium containing tissue.

13. The method of claim 10 wherein the S-polymer is mixed with a portion of bone graft.

14. The method of claim 10 wherein the S-polymer is infused into a spongy portion of tissue.

* * * * *